(12) United States Patent
Fleischer et al.

(10) Patent No.: US 8,570,520 B2
(45) Date of Patent: Oct. 29, 2013

(54) OPTICAL MEASURING CELL AND GAS MONITOR

(75) Inventors: Maximilian Fleischer, Höhenkirchen (DE); Uwe Lampe, Buxtehude (DE); Rainer Strzoda, München (DE)

(73) Assignee: Siemens Aktiengesellschaft, München (DE)

(*) Notice: Subject to any disclaimer, the term of this patent is extended or adjusted under 35 U.S.C. 154(b) by 400 days.

(21) Appl. No.: 12/516,008

(22) PCT Filed: Nov. 19, 2007

(86) PCT No.: PCT/EP2007/062481
§ 371 (c)(1),
(2), (4) Date: Jan. 7, 2010

(87) PCT Pub. No.: WO2008/061949
PCT Pub. Date: May 29, 2008

(65) Prior Publication Data
US 2010/0149538 A1 Jun. 17, 2010

(30) Foreign Application Priority Data

Nov. 22, 2006 (DE) .............. 10 2006 055 157

(51) Int. Cl.
*G01N 21/00* (2006.01)
(52) U.S. Cl.
USPC ........................................ 356/437
(58) Field of Classification Search
USPC ........................ 356/432–440, 246
See application file for complete search history.

(56) References Cited

U.S. PATENT DOCUMENTS

| 5,777,735 | A | 7/1998 | Reagen | |
|---|---|---|---|---|
| 6,603,556 | B2 * | 8/2003 | Belz et al. | 356/440 |
| 6,748,334 | B1 | 6/2004 | Perez et al. | |
| 7,531,470 | B2 * | 5/2009 | Brody | 438/800 |
| 7,961,325 | B2 * | 6/2011 | Palmskog et al. | 356/433 |
| 2003/0107739 | A1 * | 6/2003 | Lehmann et al. | 356/437 |
| 2004/0263843 | A1 | 12/2004 | Knopp | |
| 2005/0063869 | A1 | 3/2005 | Follonier | |
| 2006/0192967 | A1 * | 8/2006 | Kluczynski | 356/439 |
| 2008/0230687 | A1 * | 9/2008 | Kampf | 250/282 |
| 2008/0231857 | A1 * | 9/2008 | Depeursinge et al. | 356/437 |

FOREIGN PATENT DOCUMENTS

| DE | 102005016320 A1 | 10/2006 |
|---|---|---|
| EP | 1653216 A2 | 5/2006 |
| JP | 11295213 A | 10/1999 |
| JP | 2000146832 A | 5/2000 |

(Continued)

OTHER PUBLICATIONS

Rebecca L. Kozodoy et al, "Small-Bore Hollow Waveguide Infrared Absorption Cells for Gas Sensing", Applied Spectroscopy, vol. 50, No. 3, 1996, pp. 415-417.*
Gregory J. Fetzer et al, "Tunable Diode Laser Absorption Spectroscopy in Coiled Hollow Optical waveguides", Applied Optic, vol. 41, No. 18, Jun. 20, 2002, pp. 3613-3621.*

(Continued)

*Primary Examiner* — Hoa Pham

(57) ABSTRACT

An optical measuring cell for measuring gas absorption with a light source for introducing light into a measuring volume and a light sensor located approximately opposite the light source in the direction of light propagation and relative to the measuring volume for receiving light that is guided through the measuring volume is provided. The concentration of one or multiple target gases in the measuring volume is detected by an evaluation unit. The measuring volume is constituted by an internal volume of a hollow fiber having an internal diameter less than 1 mm.

4 Claims, 1 Drawing Sheet

(56) References Cited

FOREIGN PATENT DOCUMENTS

| | | |
|---|---|---|
| JP | 2000193583 A | 7/2000 |
| JP | 2001330540 A | 11/2001 |
| JP | 2001110698 A | 12/2001 |
| JP | 2002107299 A | 4/2002 |
| JP | 2002526763 A | 8/2002 |
| JP | 2002296175 A | 10/2002 |
| JP | 2003207442 A | 7/2003 |
| JP | 2006125919 A | 5/2006 |
| JP | 2007506978 A | 3/2007 |
| WO | 9832003 A1 | 7/1998 |
| WO | WO 0064492 A1 | 11/2000 |
| WO | WO 2005031354 A2 | 4/2005 |
| WO | WO 2006033635 A1 | 3/2006 |

OTHER PUBLICATIONS

Mordkovich et al, "The Large-Scale Production of Hydrogen from Gas Mixtures: A Use for Ultra-Thin Palladium Alloy Membranes", International Journal of Hydrogen Energy, Elsevier Science Publishers B.V., Barkind GB, , Jul. 1, 1993, pp. 539-544, vol. 18, Nr 7.

Docquier et al., "Combustion control and sensors: a review", Progress in Energy and Combustion Science, Elsevier Science Publishers, Amsterdam, Jan. 1, 2002, pp. 107-150, vol. 28, Nr 2.

Communication from European Patent Office listing cited references, Nov. 8, 2011, pp. 1-p.

T. Ritari et al.; "Gas sensing using air-guiding photonic bandgap fibers"; Optics Express, Optical Society of America, Washington, DC; Aug. 23, 2004; vol. 12, No. 17; pp. 4080-4087.

\* cited by examiner

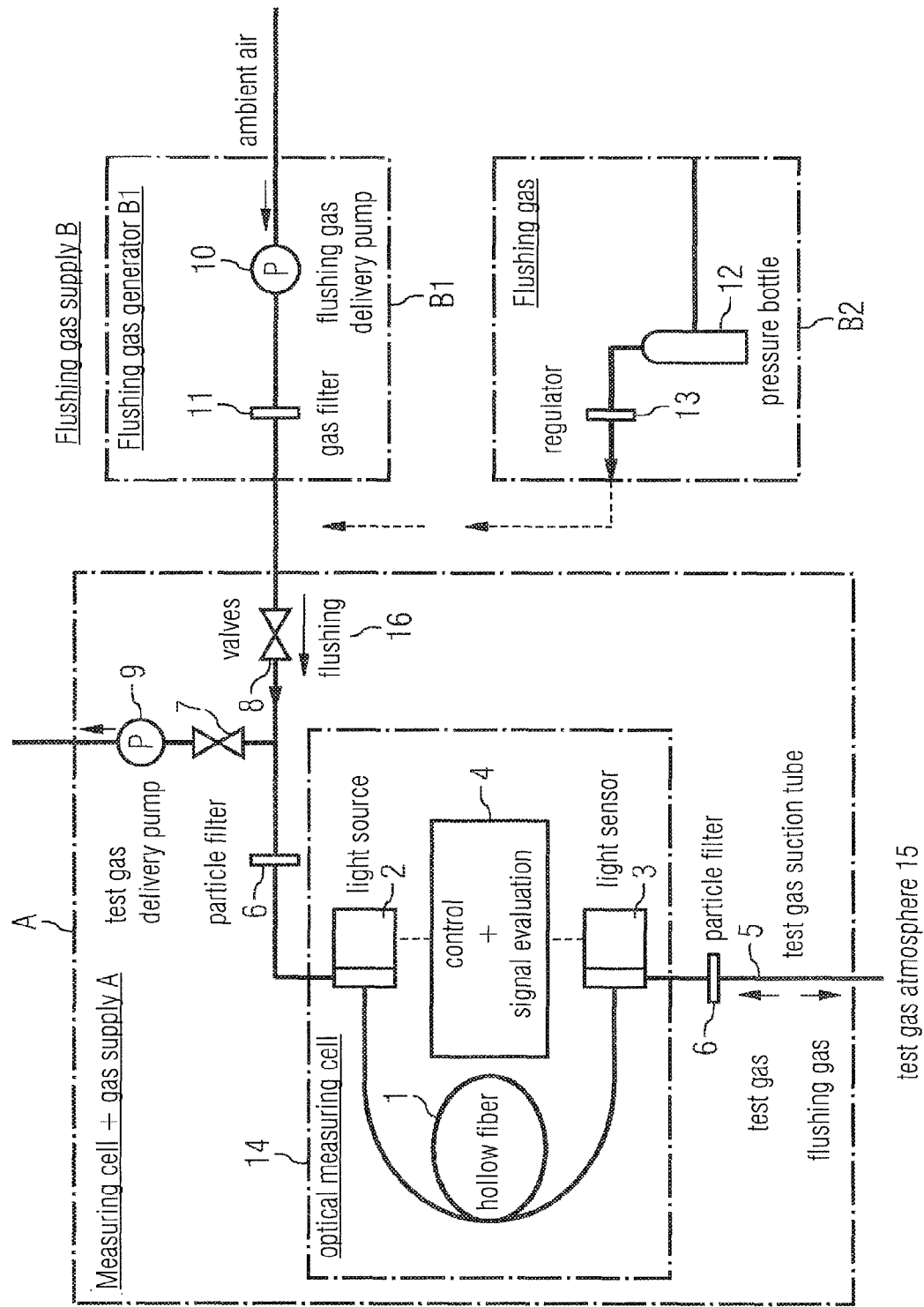

OPTICAL MEASURING CELL AND GAS MONITOR

CROSS REFERENCE TO RELATED APPLICATIONS

This application is the US National Stage of International Application No. PCT/EP2007/062481 filed Nov. 19, 2007 and claims the benefit thereof. The International Application claims the benefit of German Patent Application No. 10 2006 055 157.5 DE filed Nov. 22, 2006, both of the applications are incorporated by reference herein in their entirety.

FIELD OF INVENTION

The invention relates to an optical measuring cell and a gas monitor for gas absorption methods, and a gas monitor.

BACKGROUND OF INVENTION

In the fields of photometry and optical spectroscopy to determine the concentration of a gas component in a test gas by means of absorption measurement, the problem arises with the measuring sample cell that the transmission of the empty sample cell without any target gas present, and therefore without any absorption due to the target gas, must be known in order to be able to identify the target gas by evaluating the gas-dependent absorption.

A known solution consists in flushing the sample cell with a gas from a reservoir, for example a compressed gas bottle, which does not contain the gas components to be measured and also does not absorb in the wavelength region being used. Nitrogen, for example, is usable for this purpose if ambient air is used as the test gas. Since conventional measuring cells usually have large volumes, depending on their application, being typically >100 cm$^3$ to several liters, and a flushing gas volume which is a multiple of the measuring cell volume is needed for each flushing operation, then for continuously running or large numbers of measuring processes, this results in a substantial consumption of gas.

SUMMARY OF INVENTION

It is an object of the invention, in order to provide a stable calibration level for an optical gas sensor system with, for example, pre-determined wavelengths and a non-scanning system, to describe a measuring path which is independent of changes/soiling in the optical measuring system or the measuring sample cell and which is characterized by having the smallest possible test gas volume.

The solution is provided by an optical measuring cell and a gas monitor as claimed in the independent claims.

Advantageous embodiments are contained in the dependent claims.

In order to measure the gas-dependent absorption, at least one hollow fiber is used, having a diameter typically in the sub-millimeter region. Both the gas being tested and the light used for the absorption measurement are fed into the core of the hollow fiber which is open at the front face. Coupling in of the light takes place in the longitudinal direction of the hollow fiber. Due to the oblique reflection angles occurring therein, even with the hollow fiber, particularly a glass fiber, tightly bent, the light can be guided for several meters without significant loss.

Using hollow fibers, the particular advantage of a long absorption path is obtained, coupled with a sensitive detection of gas, as well as small measuring cell volumes. For example, a meter length of a hollow fiber with a diameter of 0.5 mm has a volume of approximately 0.2 cm$^3$. Therefore only a few cm$^3$ of flushing gas is required to flush such a fiber. A 3-liter bottle of flushing gas with a pressure of 200 bar used for repetitive measurements on a 10-minute cycle and with a gas consumption of approximately 1 cm$^3$ per flush would be able to supply the measuring apparatus with flushing gas for over ten years. A self-sufficient measuring apparatus can therefore be realized which could last for all its service lifetime without replenishment of consumable media, for example, for flushing.

It is advantageous to replace the flushing gas supply B, comprising a reservoir B2 such as a compressed gas bottle, by a flushing gas generator B1 wherein the flushing gas is directly generated in a cleaning procedure. Theoretically, the design then consists of the optical measuring cell 14 and the flushing gas generator B1, which itself essentially consists of a gas supply pump 10 and a gas filter 11.

The invention consists essentially in the combination of the use of a hollow fiber with its typical volume as the optical measuring cell. This depends on the fiber length and is usually in the range of less than or equal to 1 cm$^3$ per meter of fiber length, as a result of which low demands are made on the quantity of flushing gas required when totaled over many flushing cycles. The demands made on the flushing gas supply can be met with gas bottles or flushing gas generators of small volume capacity, as described above.

Where gas measurements are made over a long period of time, the advantage arises that for a considerable period, no refilling of the supply of auxiliary gas/flushing gas for the measuring apparatus is necessary where a compressed gas bottle is used for supplying flushing gas. This results in the possibility of providing self-sufficient gas monitors which require minimal maintenance with regard to the auxiliary gas. Due to the compact components, such as hollow fiber and flushing gas generator, highly sensitive portable gas monitors can also be realized using this measuring principle.

BRIEF DESCRIPTION OF THE DRAWING

The invention will now be described with the aid of non-restrictive exemplary embodiments, making reference to the accompanying drawing:

FIGURE shows a measuring cell.

DETAILED DESCRIPTION OF INVENTION

The FIGURE shows a measuring cell with a gas supply A, comprising an optical measuring cell 14 with a hollow fiber 1.

The FIGURE shows an exemplary embodiment of the invention in detail. The arrangement comprises the optical measuring cell 14, the test gas delivery system and the flushing gas delivery system as well as a flushing gas supply. The optical measuring cell comprises the hollow fiber 1 as the absorption measuring cell with the light source 2, the light detector 3 and the control and evaluation circuit 4.

The test gas delivery system comprises the test gas suction tube 5, optional fine-pored particle filters 6 and, following the hollow fiber 1, a valve 7 before the test gas delivery pump 9, as well as a gas outlet. A valve 8 closes off the measuring cell with the gas delivery A in the direction toward the flushing gas supply B. The flushing gas supply can comprise a compressed flushing gas bottle B2. However, the use of a flushing gas supply using a flushing gas generator B1 which generates a flushing gas and which contains none of the gas to be detected during measuring is advantageous. The flushing gas generator B1 comprises the gas delivery pump 10 and the actual gas generator. Alternatively, the flushing gas generator comprises a flushing gas reservoir, for example, a pressurized gas bottle 12 with the regulating valve 13 for setting the gas flow.

Sequence of the Measuring Cycle:

Flushing cycle: the flushing gas pump 10 is in operation and the valve 8 is opened, whilst the valve 7 is closed. The test gas delivery pump 9 is switched off. The flushing gas flows through the hollow fiber 1 and flushes the test gas residue back into the test gas atmosphere 15. Following a sufficient flushing time, an optical absorption measurement is carried out, initially the calibration measurement, which is performed with a volume of flushing gas in the hollow fiber.

Measuring cycle: the valve 8 is closed, the valve 7 is opened, the flushing gas pump 10 is switched off and the test gas pump 9 is put into operation. Now the test gas flows through the hollow fiber 1 and an optical transmission measurement is carried out. The ratio of the transmission with test gas to that with flushing gas (calibration measurement) gives the gas-dependent transmission, dependent on the fundamental transmission of the absorption path, the hollow fiber. The procedure is similar when the flushing gas is provided from a compressed gas bottle 12.

In the exemplary embodiment, test gas and flushing gas flow through the measuring fiber in contrary directions. By reversing the delivery direction of the test gas delivery pump, it is possible to have both gases flow through the hollow fiber in the same direction.

Example for Flushing Gas Generators:

1. If the gas concentration measurement takes place, for example, in a hydrogen atmosphere, the gas filter is a heated palladium membrane, which is comparable with a Pd diffusion cell. The required pressure difference is provided by a gas delivery pump. The contaminated hydrogen is fed to the filter. Since only protons can diffuse through Pd, on the secondary side pure hydrogen, which can be used as the flushing gas, is produced.

2. If the measurement takes place in air or in an oxygen atmosphere, a pump cell which conducts oxygen ions, such as zirconium oxide at 600° C., suggests itself as the oxygen supplier. A voltage is applied across the primary side and the secondary side of the heated zirconium ceramic material, which leads to oxygen transport through the ceramic material. On the secondary side pure oxygen, which can be used as the flushing gas, is produced. No extra pump is required with this embodiment, since the pump action is contained in the principle of the cell. According to this principle, the reference gas oxygen can also be generated through the electrochemical decomposition of other oxygen-containing gases, such as $H_2O$, $CO_2$, $CO$, $NO$, $NO_2$.

3. Oxygen or hydrogen can be produced in the liquid phase by electrolysis of acidified water. Depending on the gas required, the gas produced either at the cathode or the anode can be used for flushing. The electrolysis is only started when flushing gas is needed. An electrolysis cell and possibly a gas delivery pump are required. A unit of this type can be operated over several years if only the aforementioned small quantities of flushing gas are needed.

4. The small quantities of flushing gas needed for the flushing process can be produced in the required quantity and purity by known chemical reactions. Examples of such methods for the production of flushing gases are:

4a. Production of Hydrogen:
Dissolving aluminum or silicon in a concentrated alkali solution

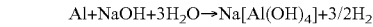

$$Al+NaOH+3H_2O \rightarrow Na[Al(OH)_4]+3/2H_2$$

The reaction is started by adding the Al to the sodium hydroxide solution. Once a sufficient quantity of gas has been generated, the feeding in of Al is stopped. The apparatus consists of respective supply containers for the NaOH and the Al in the form, for example, of filings, a dosing apparatus for the aluminum filings and a gas delivery pump. Depending on the chemical supplies and the number of flushing cycles, the apparatus can supply flushing gas for several years.

4b. Production of Nitrogen:
Air is passed over glowing copper, by means of which the oxygen can be entirely removed. What remains is a mixture of nitrogen with 1% argon (which has no interfering effect). Apart from the Cu and the heater for the Cu, a gas delivery pump is also required. The procedure is only started when the measuring cell is to be flushed. Maintenance is required essentially only to replace the copper. Depending on the number of flushing cycles and the gas quantity needed, the apparatus can be used for several years without maintenance.

4c. Production of Oxygen:
Oxygen can be produced in precisely calculable quantities by dropwise addition of potassium permanganate solution to a solution of hydrogen peroxide acidified with sulfuric acid. Two supply containers are needed for the chemicals, which are dosed into a reaction vessel, and a gas delivery pump. The procedure can take place as follows:

When flushing is to be started, a volume of hydrogen peroxide corresponding to the desired oxygen quantity is placed in the reaction vessel and the potassium permanganate is added dropwise.

An alternative method of producing oxygen is the decomposition of potassium chlorate or potassium permanganate by heating. At the start of the flushing procedure, the chemical is heated for long enough until a sufficient quantity of the gas has been generated. Then the process is stopped by cooling. Only the supply vessel, possibly a reaction vessel, a dosing device for the chemicals and a gas delivery pump are required. Only the supply of chemicals has to be topped up, their quantity determining the maintenance time intervals.

5. Cleaning air with adsorption traps for water and carbon dioxide: water vapor can be removed from the air stream by passing the air through desiccants (silica gel or $CaCl_2$). $CO_2$ can be removed from the air by reaction with CaO. Only the chemical containers and a gas delivery pump are needed. The apparatus for drying the gas can be regenerated by simple heating, whilst the CaO is consumed and must be topped up. The maintenance interval depends on the size of the chemical supplies and the flushing gas requirement.

Due to the low volume of the measuring cell and the small quantity of flushing gas as a consequence of the use of a hollow fiber as the optical measuring cell, the flushing gas generator can also be made compact. This enables the realization of gas monitors in a compact form, since not only the gas absorption measuring cell, but also the flushing gas supply, can be constructed small.

The invention claimed is:
1. An optical measuring cell for a gas absorption measurement, comprising:
a light source for introducing light into a measuring volume;
a light sensor configured to detect light conducted through the measuring volume, the light sensor being arranged approximately opposing the light source in relation to the measuring volume and in the direction of propagation of the light source;

an evaluation unit configured to determine a concentration of one or more target gases in the measuring volume, a gas delivery device for supplying the measuring volume with a flushing gas, wherein the gas delivery device supplies the flushing gas from a flushing gas generator, and wherein the flushing gas is directly generated in a cleaning procedure, wherein the flushing gas generator comprises a gas filter which is a heated palladium membrane and a gas delivery pump, or a pump cell which conducts oxygen ions, wherein a voltage is applied across a primary side and a secondary side of the pump cell which includes heated zirconium ceramic material, wherein the voltage leads to oxygen transport through the pump cell; and a hollow fiber, wherein the measuring volume is represented by an internal volume of the hollow fiber, the hollow fiber having an internal diameter of less than 1 mm.

2. The optical measuring cell as claimed in claim 1, wherein inner surfaces of the hollow fiber are configured to be light-reflecting.

3. The optical measuring cell as claimed in claim 1, wherein the flushing gas generator generates the flushing gas by one or more chemical reactions.

4. The optical measuring cell as claimed in claim 3, wherein the flushing gas comprises a gas or a gas mixture which is not a gas to be detected in a target gas measurement.

* * * * *